US00PP17749P3

(12) United States Plant Patent
Beckman

(10) Patent No.: US PP17,749 P3
(45) Date of Patent: May 22, 2007

(54) **PINEAPPLE LILY PLANT NAMED '*EUCOMIS* 155'**

(50) Latin Name: *Eucomis vandermerwei*
Varietal Denomination: ***Eucomis* 155**

(75) Inventor: Peter Beckman, Santa Cruz, CA (US)

(73) Assignee: Golden State Bulb Growers, Watsonville, CA (US)

( * ) Notice: Subject to any disclaimer, the term of this patent is extended or adjusted under 35 U.S.C. 154(b) by 0 days.

(21) Appl. No.: 11/214,263

(22) Filed: Aug. 29, 2005

(65) Prior Publication Data

US 2007/0050872 P1 Mar. 1, 2007

(51) Int. Cl.
*A01H 5/00* (2006.01)

(52) U.S. Cl. ..... Plt./263

(58) Field of Classification Search ..... Plt./263, Plt./313

See application file for complete search history.

*Primary Examiner*—Kent Bell
(74) *Attorney, Agent, or Firm*—Jondle & Associates P.C.

(57) ABSTRACT

A pineapple lily plant particularly distinguished by a short, compact plant habit, a short flower stalk, deep purple-lavender flowers, and floriferousness is described.

1 Drawing Sheet

Genus and species: *Eucomis vandermerwei.*
Variety denomination: '*Eucomis* 155'.

BACKGROUND OF THE NEW PLANT

The present invention comprises a new and distinct cultivar of pineapple lily, botanically known as *Eucomis vandermerwei,* and hereinafter referred to by the cultivar name '*Eucomis* 155'. The new cultivar was an individual selection, asexually reproduced from vegetative cuttings and tissue culture resulting from the cross of a single plant of the female parent, *Eucomis vandermerwei* (unpatented), and the male parent, an individual plant of *E. vandermerwei* 'Hawkfall Hybrids' (patent status unknown).

'*Eucomis* 155' is a product of a planned breeding program intended to create new pineapple lily plants that are short, compact, fragrant, and brightly colored.

The new cultivar was created in Moss Landing, Calif., and has been asexually reproduced repeatedly by vegetative cuttings and tissue culture in Moss Landing, Calif. for two or more generations. The present invention has been found to retain its distinctive characteristics through successive propagations.

SUMMARY OF THE INVENTION

The following are the most outstanding and distinguishing characteristics of this new cultivar when grown under normal horticultural practices in a brightly lit greenhouse or in an open field.

1. A short plant with a compact and full plant habit;
2. A short flower stalk;
3. Fragrant;
4. Bright and deeply saturated purple-lavender flowers; and
5. Principally plain glossy foliage (with a very faint stippled overlay at the bottom under-third of the leaf).

DESCRIPTION OF PHOTOGRAPH

This new pineapple lily plant is illustrated by the accompanying photograph which show blooms, buds, and foliage of the plant. The colors shown are as true as can be reasonably obtained by conventional photographic procedures.

The accompanying photograph shows the overall plant habit, foliage, immature blooms, and mature blooms.

DESCRIPTION OF THE NEW CULTIVAR

The following detailed descriptions set forth the distinctive characteristics of '*Eucomis* 155'. The data that define these characteristics were collected from asexual reproductions carried out in Moss Landing, Calif. The plant history was taken on two-year-old plants based on a 2–2.25 inch-diameter bulb under Moss Landing, Calif. summer conditions. Color references are primarily to The R.H.S. Colour Chart of The Royal Horticultural Society of London (R.H.S.) (2001).

DETAILED BOTANICAL DESCRIPTION

Classification:

*Botanical.*—*Eucomis vandermerwei*×'Hawkfall Hybrids'.

*Common name.*—Pineapple lily.

*Parentage.*—Female parent: An unnamed plant of *Eucomis vandermerwei* (unpatented). Male parent: *Eucomis vandermerwei* 'Hawkfall Hybrids' (patent status unknown).

Size:

*Form.*—Compact with leaves arranged more or less symmetrically below the flower stocks; the overall effect of the flower stock is columnar with a topknot of leaves, somewhat like a pineapple.

*Height above the soil.*—4.0–13.0 inches for a 2–2.25 inch bulb, depending on greenhouse conditions.

*Height of top of inflorescence above the soil.*—6.0–13.0 inches depending on growing conditions.

*Diameter of plant.*—4.0–9.0 inches.

Stems:

*Length.*—5.0–13.0 inches.

*Diameter.*—¼–½ inches.

*Color.*—RHS 138C (medium-green) to RHS 138B (medium-green) with purple speckling up the entire stem to just below the florets.

*Texture.*—Smooth.

Leaves:

*Arrangement.*—More or less symmetrical below the flower stalks; leaves arise from a common base meristem as in a true bulb, where some bulbs in larger sizes have multiple base meristems.

*Quantity.*—Varies, but 16–25 is typical of a 2-inch bulb grown under bright greenhouse conditions.

*Size.*—Width: 1¼–2½ inches. Length: 4.0–9.0 inches in direct sunlight, but shaded plants and larger bulbs have longer leaves.

*Shape.*—Lanceolate.

*Color.*—Upper surface: RHS 137A (green) to RHS 137B (green) with an RHS 59D (slight purple) margin. Lower surface: RHS 137A (green) to RHS 137B (green) with an RHS 59D (slight purple) margin; at bottom third of the leaf base, there is faint stippling.

*Apex.*—Acute.

*Base.*—Contiguous with lanceolate leaf.

*Margin.*—Entire and continuous with a slight undulation of the edge.

*Venation.*—Parallel with slightly impressed central vein.

*Surface texture.*—Smooth and slightly glossy.

Topknot:

*Size.*—Individual leafy bracts are 1.0–1.5 inches in length and ¼–⅜ inches in width, making the topknot approximately 2.0–3.0 inches in both diameter and height.

*Color.*—RHS 137A to RHS 137B with an RHS 59D (slight purple) margin.

*Form.*—Leafy bracts of 10 to 30 bracts are arranged more or less symmetrically, radiating from the apex and resembling a pineapple topknot atop the inflorescence stalk.

*Individual leafy bract descriptors.*—Essentially leaf-like, but miniature; the overall shape is lanceolate, the apex is apiculate and the base is attenuate; the margin is entire, continuous and largely smooth and no more than 10% of the leafy bracts have an RHS 59D (purple) margin from the base to the bract tip.

Bulb:

*Size.*—1.5–3.5 inches in diameter for a flowering and marketable bulb.

*Color.*—RHS 200A to RHS 200C (brown) outer leaf scales.

*Shape.*—Non-tunicate (typical of an onion-type, true bulb form).

Inflorescence:

*Time to produce a finished flowering plant.*—85–110 days.

*Number of flowers per bulb.*—One or more inflorescences depending on the bulb size.

*Lastingness of individual flowers on the plant.*—7–21 days.

*Fragrance.*—Similar to that of coconut oil.

Bud:

*Form.*—Elliptic (pomegranate seed-like).

*Size.*—¼–⅝ inch in length and ¼–⅜ inch in width.

*Color.*—A deep glossy purple-lavender, RHS 59A to RHS 59B.

Flower:

*Form.*—Individual flowers are clustered symmetrically around the top 33%–50% of one-to-multiple inflorescences protruding at foliage level even with foliage; flowers open from the bottom to the top of the stem.

*Diameter.*—Individual flowers are ½ to ¾ inch when open and clustered around the stalk.

*Inflorescence.*—Typically from 9–15 inches in height and 1½–2¼ inches in width.

*Perianth lobes.*—Number: 6 perianth lobes. Color: Upper surface: RHS 59A to RHS 59B on younger flowers and RHS 59D to RHS 60D for older flowers. Lower surface: RHS 59A to RHS 59B on younger flowers and RHS 59D to RHS 60D for older flowers, but slightly darker. Shape: Ovate. Apex: Acute. Base: Broad. Margin: Straight, smooth and entire. Texture: Smooth.

Reproductive organs:

*Androecium*—Number of anthers: 6. Filament color: RHS 58D (red-purple) at base to 59D (red-purple) at tip. Filament length: ¼–⅜ inch. Pollen color: RHS 4A to RHS 5B (pale yellow to ivory). Pollen amount: Slight.

*Gynoecium.*—Pistil number: 1. Pistil length: ⅛–⅜ inch. Stigma color: RHS 59D to RHS 60D (red-purple). Stigma shape: Cone-shaped. Style color: RHS 158D (yellow-white) to RHS 155D from base to tip. Style length: 3/32–1 1/32 inch. Style shape: Pyramidal cone.

Fruit/seed set: At maturity, the plant sets a dried, papery, flower-sized pod holding one to multiple seeds.

Disease and insect resistance: Pests and diseases are few; mealybugs can occasionally harbor deep in the bulb scales; *Pythium* can attack roots.

COMPARISON WITH KNOWN CULTIVARS

Cultivars '*Eucomis* 155' differs from the female parent, an unnamed individual plant of *Eucomis vandermerwei* (unpatented) in that '*Eucomis* 155' has more leaves that are ½ to 4½ inches longer. The deep green leaves of '*Eucomis* 155' have slight purple margins on front and back, while the leaves of the female parent have heavy blackish-mauve and russet marks on the front and back of the leaves, and have a matte-finish. The flower color of '*Eucomis* 155' is brighter with a more saturated lavender, and the stems are dotted with purple-lavender marks rather than the deep blackish-mauve and burgundy spots of the female parent. Additionally, '*Eucomis* 155' is more floriferous than the female parent, having one or more flowers per bulb.

Cultivar 'Eucomis 155' differs from the commercial comparison variety, a typical unnamed plant of *Eucomis cosmosa* (unpatented) in that '*Eucomis* 155' has shorter stems and leaves, and the flower stem is half as long as that of a typical unnamed plant of *Eucomis cosmosa*. Additionally, '*Eucomis* 155' has bright, deeply saturated purple-lavender flowers while a typical unnamed plant of *Eucomis cosmosa* has creamy pink flowers.

Cultivar '*Eucomis* 155' differs from the male parent (patent status unknown) in that '*Eucomis* 155' is more floriferous and has a darker and more saturated purple flower color than the male parent.

I claim:

1. A new and distinct cultivar of *Eucomis* plant as shown and described herein.

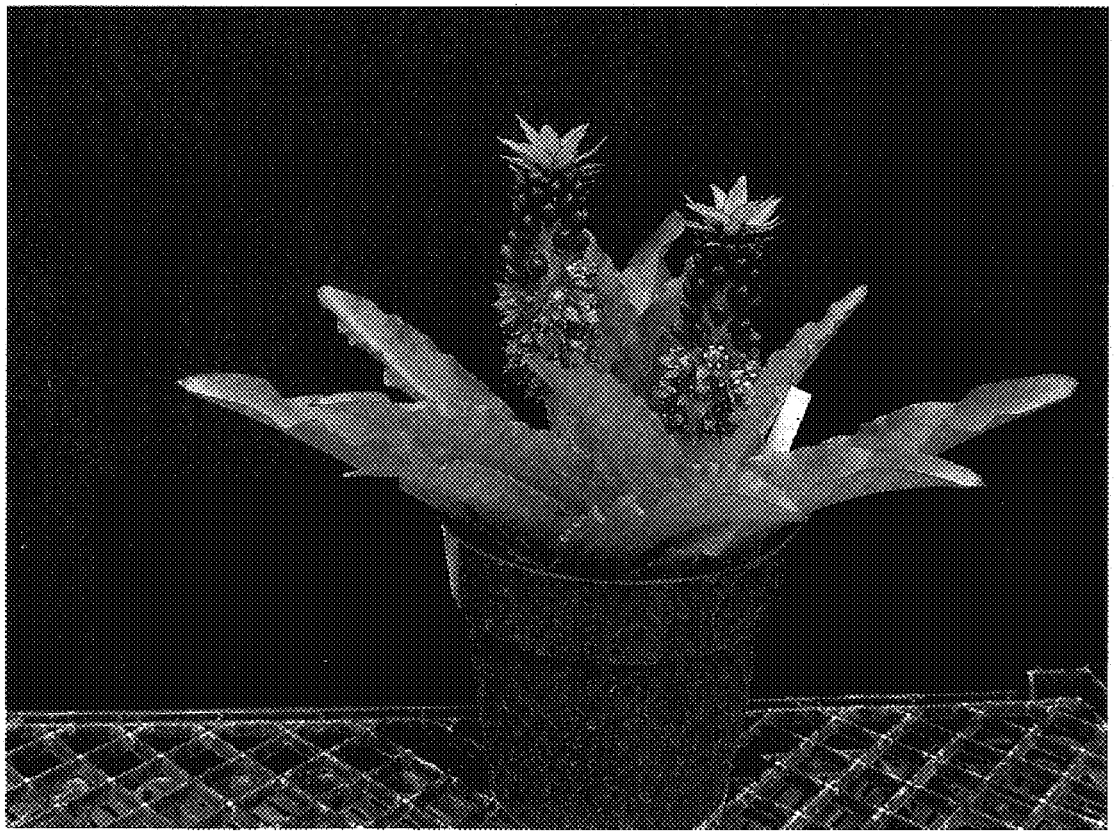

* * * * *